(12) United States Patent
Shah et al.

(10) Patent No.: US 9,718,777 B2
(45) Date of Patent: Aug. 1, 2017

(54) PROCESS FOR THE PREPARATION OF HIGH PURITY MIGLUSTAT

(71) Applicants: Shrenik K. Shah, Metuchen, NJ (US); Raju Mahadev Kharatkar, Baroda (IN); Chiragkumar Anilkumar Bhatt, Bharuch (IN); Jitendra Bhagwandas Kevat, Baroda (IN)

(72) Inventors: Shrenik K. Shah, Metuchen, NJ (US); Raju Mahadev Kharatkar, Baroda (IN); Chiragkumar Anilkumar Bhatt, Bharuch (IN); Jitendra Bhagwandas Kevat, Baroda (IN)

(73) Assignee: Navinta, LLC, Ewing, NJ (US)

( * ) Notice: Subject to any disclaimer, the term of this patent is extended or adjusted under 35 U.S.C. 154(b) by 0 days.

(21) Appl. No.: 14/965,436

(22) Filed: Dec. 10, 2015

(65) Prior Publication Data

US 2016/0168092 A1    Jun. 16, 2016

Related U.S. Application Data

(60) Provisional application No. 62/090,783, filed on Dec. 11, 2014.

(51) Int. Cl.
| | |
|---|---|
| *C07H 15/00* | (2006.01) |
| *C07H 17/00* | (2006.01) |
| *C07G 3/00* | (2006.01) |
| *C07D 211/46* | (2006.01) |
| *C07H 1/00* | (2006.01) |
| *C07H 5/04* | (2006.01) |
| *C07H 5/06* | (2006.01) |

(52) U.S. Cl.
CPC .............. *C07D 211/46* (2013.01); *C07H 1/00* (2013.01); *C07H 5/04* (2013.01); *C07H 5/06* (2013.01)

(58) Field of Classification Search
None
See application file for complete search history.

(56) References Cited

U.S. PATENT DOCUMENTS

| 4,639,436 A | 1/1987 | Junge et al. | |
|---|---|---|---|
| 8,802,155 B1* | 8/2014 | Attolino | C07H 5/06 424/489 |
| 2014/0205666 A1 | 7/2014 | Attolino et al. | |
| 2014/0243369 A1 | 8/2014 | Attolino et al. | |

OTHER PUBLICATIONS

Brittain, Harry G., ed. Polymorphism in pharmaceutical solids. CRC Press, 2016.*
Byrn et al. Pharmaceutical Research (1995), vol. 12, pp. 945-954.*
Baxter, et al., "Expeditious Synthesis of Azasugars by the Double Reductive Amination of Dicarbonyl Sugars", J. Org. Chem. 1994,59, 3175-3185.
Wennekes, et al., "Large-Scale Synthesis of the Glucosylceramide Synthase Inhibitor N-[5-(Adamantan-1-yl-methoxy)-pentyl]-1-deoxynojirimycin", Organic Process Research & Development 2008, 12, 414-423.
Matos, et al., "Synthesis of 1-Deoxynojirimycin and N-Butyl-1-deoxynojirimycin", Synthesis 1999, No. 4, 571-573 ISSN 0039-7881 © Thieme Stuttgart—New York.

* cited by examiner

*Primary Examiner* — Patrick Lewis
(74) *Attorney, Agent, or Firm* — St. Onge Steward Johnston and Reens, LLC

(57) ABSTRACT

A process for the preparation and isolation of crystalline miglustat without the use of a column chromatography or ion exchange purification. The crystalline miglustat has a high purity and a melting point of 128° C. and an endothermic peak is 133° C.

12 Claims, 4 Drawing Sheets

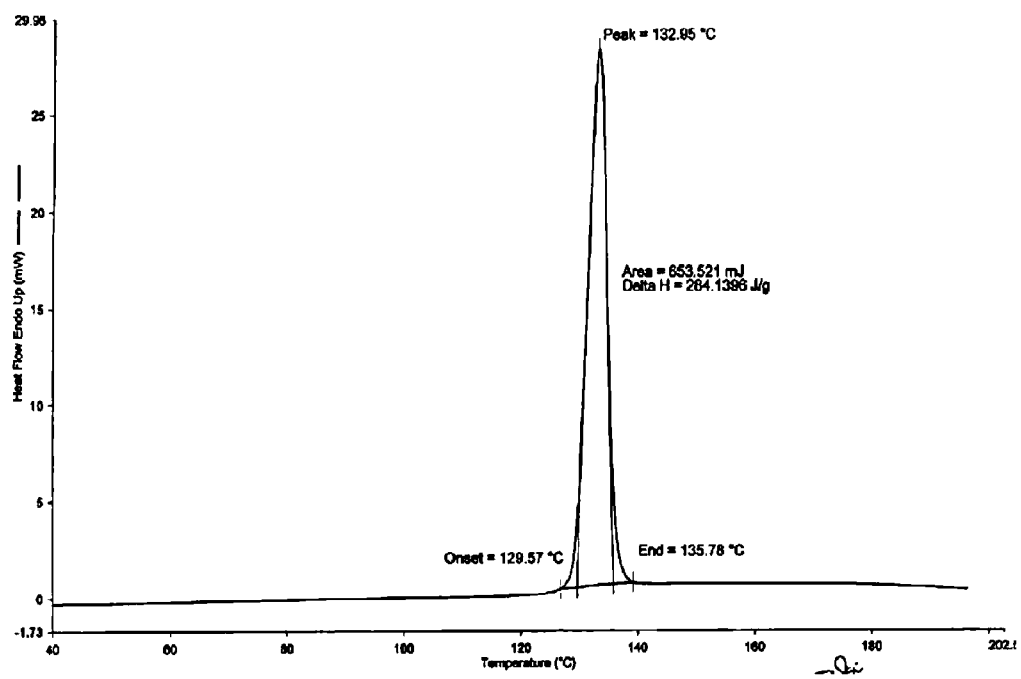
Figure 1 – DSC Thermogram of Miglustat (I)

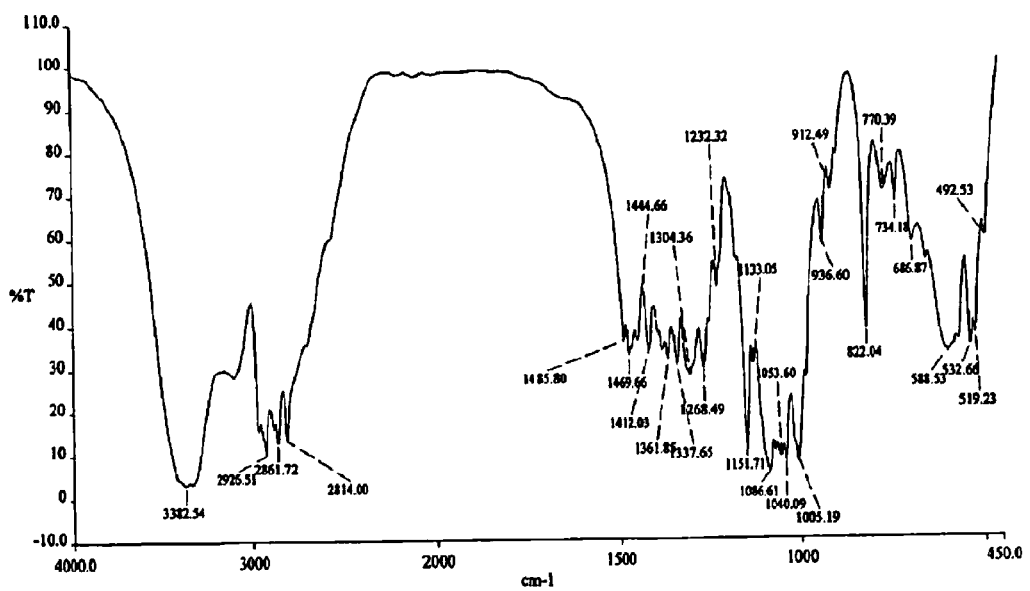
Figure 2 – FTIR Spectrum of Miglustat (I)

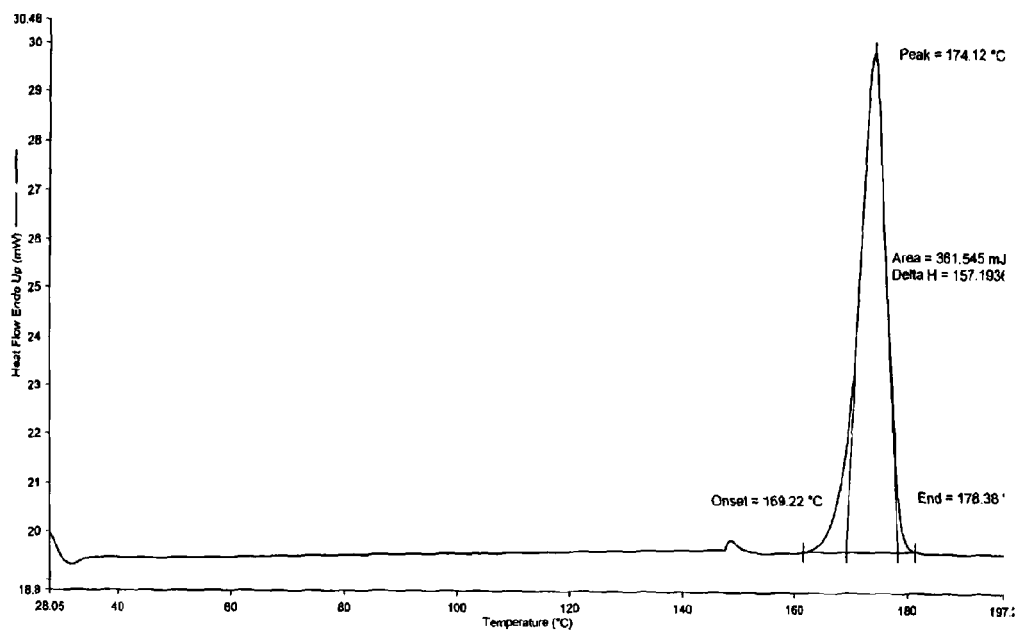
Figure 3 – DSC Thermogram of Miglustat Hydrochloride (III)

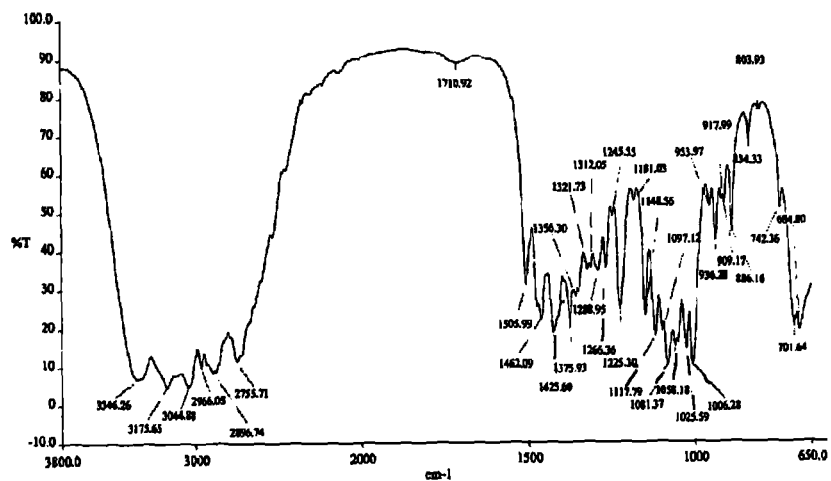
Figure 4 – FTIR Spectrum of Miglustat Hydrochloride (III)

PROCESS FOR THE PREPARATION OF HIGH PURITY MIGLUSTAT

FIELD OF THE INVENTION

The present invention relates to an improved process for the preparation of miglustat.

BACKGROUND OF THE INVENTION

Miglustat is a potent inhibitor of glycosyltransferase. It is primarily used in the treatment of Gaucher's disease. Miglustat is chemically known as N-butyl-1,5-dideoxy-1,5-imino-D-glucitol of formula (I) and is sometimes referred as N-butyl-1-deoxynojirimycin. Miglustat is a white to off-white crystalline solid with a melting point of 125-126° C. Its empirical formula is $C_{10}H_{21}NO_4$ and has a molecular weight of 219.28 g/mol.

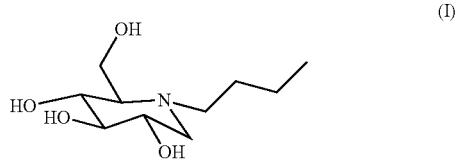

(I)

Miglustat belongs to the class of azasugars or iminosugars. Ever since the discovery of iminosugars in the 1960s, iminosugars have been subject of extensive studies in both the organic chemistry and biochemistry fields. Iminosugars are polyhydroxylated alkaloids, which may be described as monosaccharide analogues with nitrogen replacing oxygen in the ring. A well-known member of this extensive family of compounds is 1-deoxynojirimycin of formula (II).

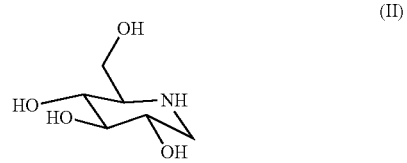 [SMILES: OCC1NCC(O)C(O)C1O]

(II)

1-Deoxynojirimycin was initially synthesized in a laboratory. Subsequently, 1-deoxynojirimycin was isolated from natural sources, such as from leaves of mulberry trees and certain species of bacteria. 1-Deoxynojirimycin was shown to be an enzyme inhibitor.

Further research on 1-deoxynojirimycin analogs revealed that N-alkylated derivatives of 1-deoxynojirimycin exhibited greater biological activity than 1-deoxynojirimycin. Among them, N-butyl-1-deoxynojirimycin or miglustat of formula (I), was identified as a very potent inhibitor of glycosyltransferase. Miglustat was later approved by the FDA for human use.

Preparation of azasugars has been a very active area of research for a long time. A seminal synthesis of the compounds of formulas (I) and (II) by double reductive aminations of 5-keto-D-glucose was developed by Baxter and Reitz (J. Org. Chem. 1994, 59, 3175). This method was later refined by Matos and Lopes (Synthesis 1999, 571), in which tetra-O-benzyl-glucose was used as a starting material. Synthesis of miglustat can be traced back to 1977, when chemists from Bayer reported a synthesis of miglustat from 1-deoxynojirimycin and patented in U.S. Pat. No. 4,639,436. Other variations of this general scheme have also appeared in patents and non-patent literature, for example, U.S. Pat. No. 8,802,155 and U.S. Application Publication No. 2014/0243369.

A major drawback of those protocols is that all of them require the use of ion-exchange resins for purification of miglustat. In those protocols, an aqueous solution of miglustat obtained after running an ion-exchange column was concentrated to isolate miglustat. Due to the presence of four hydroxyl groups and a tertiary amine moiety in its chemical structure, miglustat is extremely hydrophilic. Thus, isolation of miglustat from an aqueous solution is quite challenging. In particular, it was very difficult to remove diastereomers and inorganic impurities formed during the reactions from miglustat by those protocols. Sometimes a second chromatographic purification was required to separate these impurities from miglustat. As a result, the yields of miglustat were generally low. The requirement to use a column purification (e.g. ion exchange column, flash column chromatography) further limits the scale of miglustat that could be prepared.

Accordingly, there is a need for a robust and reproducible process for the preparation and isolation of pure miglustat on a commercial scale.

SUMMARY OF THE INVENTION

The present invention provides an improved and commercially viable process for the preparation and isolation of crystalline miglustat with a high purity.

The inventive process comprises the steps of preparing miglustat hydrochloride of formula (III) or any acid salt of miglustat, with less than 0.2% of undesired 5R product (formula IV), neutralizing the acid salt of miglustat with an organic base, crystallizing the neutralized miglustat from a medium by using an organic base in a solvent, followed by adding an anti-solvent, and collecting crystalline miglustat. The resulting crystalline miglustat has a high purity such that no ion exchange column or flash column chromatography is used to further purify the crystalline miglustat.

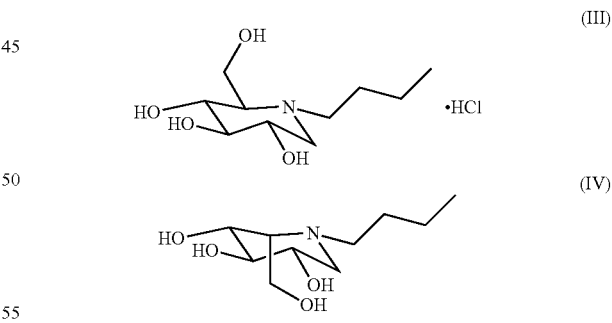

The crystalline miglustat prepared by the present invention has a high purity (i.e., with less unwanted diastereomers and other inorganic impurities) and a melting point of 128° C., which is higher than the reported melting point of miglustat of 125-126° C. in the literature.

BRIEF DESCRIPTION OF THE DRAWINGS

FIG. 1 is a DSC thermogram of crystalline miglustat of formula (I) prepared in accordance with the present invention.

FIG. 2 is an FTIR spectrum of crystalline miglustat of formula (I) prepared in accordance with the present invention.

FIG. 3 is a DSC thermogram of miglustat hydrochloride of formula (III).

FIG. 4 is an FTIR spectrum of miglustat hydrochloride of formula (III).

DETAILED DESCRIPTION OF THE INVENTION

In one aspect, the invention provides an improved process for the preparation of miglustat of a high purity without the need to use ion exchange column or flash column chromatography purification to isolate miglustat.

In lieu of column purification, the present invention purifies and subsequently isolates miglustat by the steps of neutralization of an acid salt of miglustat with an organic base and crystallization of the neutralized miglustat from a medium. The medium comprises a solvent or co-solvent in which both the miglustat salt, the organic base and the salt thereof are highly soluble, but miglustat has very low solubility. As a result, miglustat of a high purity is crystallized out of the solvent or co-solvent, leaving the rest of the compounds in the medium.

As stated before, all of the prior art references teach the use of an ion-exchange resin column, and optionally a second chromatography column, for purification of miglustat. But purification by running columns is generally not ideal because the procedure is slow, costly, tedious, and not suitable for large scale synthesis. An ion-exchange resin column is typically run by using water as a medium. The final product, miglustat, is present in the form of an aqueous solution after an ion-exchange resin column purification. Due to four hydroxyl groups and a tertiary amine moiety in its chemical structure, miglustat is very polar and hydrophilic, which makes isolation of miglustat from the aqueous solution very challenging. Thus, purification by an ion-exchange column is not ideal. Moreover, diastereomers and inorganic impurities formed during synthesis of miglustat cannot be separated from miglustat by running an ion-exchange column. Sometimes, a second, flash column chromatography purification is necessary to produce pure miglustat at the cost of lower yield. Thus, compared to the prior art, the process of the present invention, which does not use column purification, is simpler, more cost effective, and well suited for use on an industrial scale.

Scheme 1 is a synthetic scheme of miglustat in accordance with one embodiment of the invention:

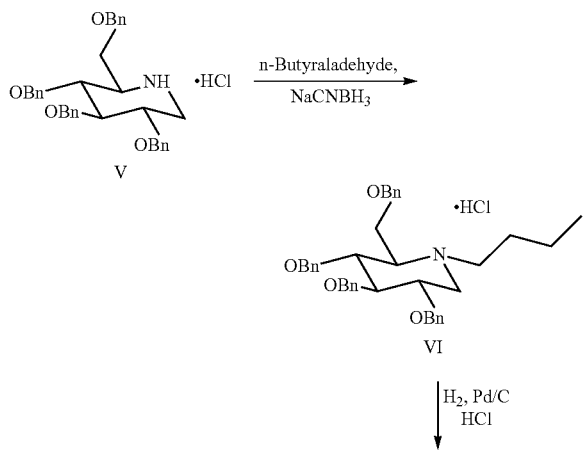

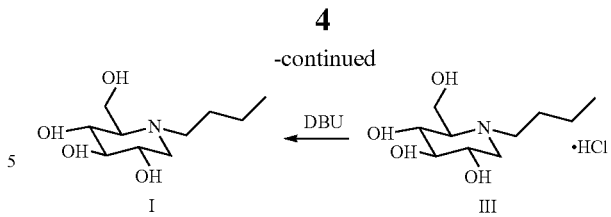

As depicted in scheme 1, the method of preparing miglustat may include the steps of: (1) providing or synthesizing a compound of formula (V); (2) conducting a reductive amination to provide a compound of formula (VI); (3) performing a hydrogenation reaction; and (4) isolating a free base miglustat.

The starting material, 2,3,4,6-tetra-O-benzyl-1-deoxynojirimycin hydrochloride of formula (V) may be prepared by following the methods described in Organic Process Research and Development, 2008, 12, 414-423.

Reaction of the compound of formula (V) with n-butyraldehyde and sodium cyanoborohydride in a suitable solvent gives 2,3,4,6-tetra-O-benzyl-N-butyl-1-deoxynojirimycin hydrochloride salt of formula (VI) (i.e., reductive amination). One novel feature of the present invention is to use a hydrochloride salt of formula (V) as a starting material for the reductive amination reaction which yields a hydrochloride salt of formula (VI) as a product. The hydrochloride salt of formula (VI) is purified and isolated in its salt form and further used in its salt form in the next step reaction. By keeping both the starting material and the product of the reductive amination as a hydrochloride salt, the reductive amination and purification are simple and highly efficient, in particular because no column purification is needed, leading to a high yield and high purity of hydrochloride salt of formula (VI) with little undesired 5R-isomer of formula (VII).

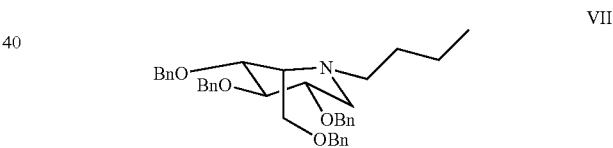

The reductive amination may be carried out by other reducing reagents known in the art, such as sodium triacetoxyborohydride, sodium borohydride, or catalytic hydrogenation. In a preferred embodiment, the reductive amination reaction is conducted as follows:

1. Add 2,3,4,6-tetra-o-benzyl-1-deoxynojirimycin hydrochloride of formula (V), n-butyraldehyde, and sodium cyanoborohydride in methanol at a temperature of about 10° to about 60° C., followed by maintaining the reaction mass temperature at about 10° to about 60° C. for about 1 to about 24 hours, preferably for about 2 to about 12 hours, and quenching the reaction with water.
2. Concentrate the reaction mass of step 1 by a rotary evaporation at a temperature of about 45° C. to about 50° C. which removes methanol.
3. Add dichloromethane into the product mixture of step 2 at a temperature of about 25° C. to about 30° C. and isolating a compound of formula (VI).

The term "concentrate" or "concentration", used herein and after, refers to a process in which a solvent is removed partially or completely by commonly used techniques, such as rotary evaporation, distillation, etc.

To the knowledge of the inventors, 2,3,4,6-tetra-O-benzyl-N-butyl-1-deoxynojirimycin hydrochloride salt of formula (VI) has never been reported as an isolated compound in literature. By the term "isolated", it means a compound exists in a definite form (e.g., solid, liquid depending on the m.p. of the compound) with greater than 90% purity. As a result of having a sufficient purity, an isolated compound shows unique NMR, IR, melting point, etc., as compared to a compound mixed with other components or dissolved in a solvent. Thus, one novel feature of the present invention is that it provides a new salt form of 2,3,4,6-tetra-O-benzyl-N-butyl-1-deoxynojirimycin, which is purified, isolated, and analytically tested. Moreover, no prior art teaches the preparation of 2,3,4,6-tetra-O-benzyl-N-butyl-1-deoxynojirimycin or its salt form via reductive amination from 2,3,4,6-tetra-O-benzyl-1-deoxynojirimycin or its hydrochloride salt form, as disclosed herein.

The hydrochloride salt form of the compound of formula (VI) is subjected to a debenzylation reaction in presence of an acid. The debenzylation reaction is conducted under a hydrogenation condition, thus the debenzylation reaction may also be called hydrogenation reaction. The debenzylation reaction is highly efficient due to the addition of an acid which increases the catalytic (e.g., 10% Pd/C) efficiency. The acid also helps the formation of miglustat in a salt form ready for subsequent isolation. Suitable acids include inorganic acid such as hydrochloric acid, hydrobromic acid, sulfuric acid, phosphoric acid, or a mixture thereof, or organic acid such as methanesulfonic acid, formic acid, toluenesulfonic acid, oxalic acid, citric acid, acetic acid, or a mixture thereof. In one embodiment, a preferred acid is hydrochloric acid and the debenzylation reaction is carried out by hydrogenation in the presence of Pd/C and hydrochloric acid to provide miglustat hydrochloride of formula (III). A person of ordinary skills in the art would understand that other hydrogenation catalysts can also be used in lieu of Pd/C.

In a preferred embodiment, the hydrogenation reaction is performed as follows:

1. Add 2,3,4,6-tetra-O-benzyl-N-butyl-1-deoxynojirimycin of formula (VI) in an alcoholic solvent, preferably methanol or ethanol.
2. Add methanolic HCl or ethanolic HCl to the reaction mixture.
3. Adjust pH of the reaction mixture to pH 0.5 to 3.0, preferably pH 1.0 to 2.0.
4. Add 10% Pd/C (50% wet) into the reaction mass followed by maintaining the reaction mass under hydrogen atmosphere at a temperature of about 10° to about 50° C., preferably about 25° to about 35° C. for about 1 to about 12 hours, preferably for about 3 to about 8 hours.
5. Concentrate the reaction mass at a temperature of about 45° to about 55° C. by rotary evaporation, followed by adding a solvent such as dichloromethane, ethyl acetate, isopropyl acetate, diethyl ether, or diisopropyl ether, and filtering to collect solid miglustat hydrochloride of formula (III).

In the final stage of the process, miglustat hydrochloride of formula (III) is dissolved in a solvent. Suitable solvents include, but are not limited to, water, methanol, ethanol, isopropanol, n-butanol, t-butanol, and a mixture of thereof. An organic base is added to liberate miglustat of formula (I), followed by crystallization of miglustat after adding an antisolvent. A skill artisan would understand that other crystallization techniques such as cooling, seeding with pure material, etc., may be used during crystallization. The crystalline solid is filtered, washed and dried to provide miglustat of a high purity.

The term "anti-solvent", used herein and after, refers to a solvent that is prone to promote crystallization of the underlying compound of interest. The organic base as well as the acid salt formed in this reaction should have good solubility in the anti-solvent, but miglustat should have low solubility in this medium (i.e., anti-solvent) so that pure miglustat can be recovered by crystallization. A suitable anti-solvent, which may also be called a second solvent, is selected from the group consisting of dichloromethane, ethyl acetate, isopropyl acetate, hexane, cyclohexane, heptane, diethyl ether, diisopropyl ether, and a mixture thereof.

Suitable organic bases include, but are not limited to, triethylamine, N,N-diisopropylethylamine, N-methylmorpholine, 1,8-diazabicycloundec-7-ene (DBU), 1,5-diazabicyclonon-5-ene (DBN). One preferred base is 1,8-diazabicycloundec-7-ene (DBU).

In a preferred embodiment, the final stage of the process is performed as follows:

1. Add miglustat hydrochloride of formula (III) and an organic base, preferably 1,8-diazabicycloundec-7-ene (DBU), into a solvent, preferably methanol, ethanol, or isopropanol, followed by maintaining the reaction mass at a temperature of about 25° C. to about 60° C., preferably about 40° C. to about 50° C. for about 30 to about 180 minutes, preferably about 90 to about 120 minutes.
2. Concentrate the reaction mass of step 1 by rotary evaporation at a temperature of about 45° C. to about 55° C. followed by adding an anti-solvent, preferably dichloromethane or ethyl acetate to form crystalline miglustat, and finally isolating the crystalline miglustat.

A novel feature of the present invention is that none of the steps (i.e., the reductive amination, the debenzylation, and the isolation of crystalline miglustat) involves the use of any traditional flash column chromatography or ion exchange column, which makes the process simpler and easier to handle, thereby increases the yield of the final product. The inventive process is particularly suitable for preparation on an industrial scale.

Another novel feature of the present invention is that the crystalline miglustat product prepared by the process of the invention has a very good purity profile. It has a purity of greater than or equal to about 99.5% and less than about 0.1% of any individual organic impurity, as measured by HPLC, and less than about 0.1% of total inorganic impurities, as evidenced by residue on ignition analysis. The crystalline miglustat product is also very pure with respect to its other isomeric impurities. For example, the undesired 5R isomeric impurity of formula (IV) is less than about 0.2%, preferably less than about 0.1%, as determined by HPLC. Moreover, the crystalline miglustat has a melting point of 128° C. and an endothermic peak is 133° C., which are higher than reported melting point and endothermic peak in the prior art. Having crystalline miglustat of a higher purity and higher melting point is beneficial in making a better drug product.

The present invention is further exemplified in detail by the following examples. However, the scope of the invention is not limited to the above description and the below examples.

Example 1

Synthesis of 2, 3, 4, 6-tetra-O-benzyl-N-butyl-1-deoxynojirimycin hydrochloride of Formula (VI)

To a solution of 2, 3, 4, 6-tetra-O-benzyl-1-deoxynojirimycin hydrochloride (V) (prepared as in Organic Process Research & Development, 2008, 12, 414-423) (45 g, 0.08 mol) in 1575 mL of methanol, n-butyraldehyde (21.6 g, 0.24 mol) and sodium cyanoborohydride (25.2 g, 0.4 mol) were added and stirred. The reaction was maintained under stirring at a temperature from about 25° C. to about 30° C. After the completion of the reaction, the reaction was quenched by adding 765 ml of 10% HCl in methanol, while keeping the temperature between 25° C. to 30° C. The reaction mass was cooled to 0° C. to 5° C. and the resulting precipitate solids were filtered. The filtrate was treated with aqueous HCl and the solid formed was filtered, suspended in 1 N HCl, stirred for 1 hour and filtered. The collected solid was washed with diisopropylether and dried under vacuum to furnish 46.2 g of compound (IV) (46.2 g, 0.075 mol, 94% yield) of high chemical purity based on HPLC analysis (>99.0%).

Example 2

Synthesis of Miglustat Hydrochloride of Formula (III)

A solution of 2, 3, 4, 6-tetra-O-benzyl-N-butyl-1-deoxynojirimycin hydrochloride (VI) (100 g, 0.16 mol) in methanol (1000 mL), 10% HCl solution in methanol (100 mL), and 10% Pd/C (50% wet) (10 g) were mixed and stirred under hydrogen atmosphere at a temperature of about 25° C. to about 30° C. until completion of the reaction. The reaction mass was filtered and the solvent was removed from the filtrate by rotary evaporation. Ethyl acetate (1000 mL) was added to the residue from the rotary evaporation to precipitate the solid. The solid was filtered and dried to isolate Miglustat hydrochloride (III) (42 g, 0.16 mol, 100% yield) of >99.5% purity as measured by HPLC analysis. The DSC thermogram of this product is provided as FIG. 3, and the FTIR spectrum of this product is provided as FIG. 4.

Example 3

Synthesis of Miglustat of Formula (I)

Miglustat hydrochloride (III) (42 g, 0.16 mol) obtained from Example 2 was dissolved in 420 mL of methanol and DBU (1,8-diazabicycloundec-7-ene) (34.1 mL) was added. The reaction mass was warmed slightly and stirred for about 2 hours. The reaction was concentrated by removal of methanol. Dichloromethane (900 mL) was added to the residue. The resulting solid was filtered and dried to obtain crystalline miglustat (I) (27 g, 0.12 mol, 75% yield) of >99.5% purity as measured by HPLC analysis. The melting point of the crystalline miglustat (I) is 128° C. The DSC thermogram and FTIR spectrum of the product are provided as FIG. 1 and FIG. 2, respectively. The crystalline miglustat (I) contained <0.05% of the 5R isomer (IV) as measured by HPLC.

As shown in Examples 1-3, the overall reaction yield from 2, 3, 4, 6-tetra-O-benzyl-1-deoxynojirimycin hydrochloride (V) to the crystalline miglustat (I) is 71%.

In another aspect, the present invention provides crystalline miglustat of formula (I) with >99.5% purity and <0.05% of the 5R isomer of formula (IV), as measured by HPLC. A unique feature of the crystalline miglustat prepared by the inventive process is that it has a melting point of 128° C., which is higher than reported melting point of miglustat (125-126° C.). A person of ordinary skill would understand a high melting point typically indicates that the product is of high purity. Another unique feature of the crystalline miglustat is that the endothermic peak is 133° C., as shown in FIG. 1, which is different from the endothermic peak at 129-132° C. as reported in U.S. Pat. No. 8,802,155. Without wishing to be bound by theory, it is believed that the inventive process produces miglustat of higher purity.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A process for the preparation of crystalline miglustat of formula (I) comprising the steps of:

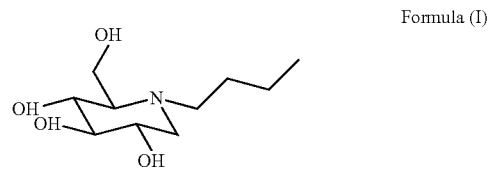

Formula (I)

(1) reacting 2,3,4,6-tetra-O-benzyl-1-deoxynojirimycin hydrochloride of formula (V) with n-butyraldehyde and sodium cyanoborohydride in an organic solvent to prepare 2, 3, 4, 6-tetra-O-benzyl-N-butyl-1-deoxynojirimycin hydrochloride of formula (VI);

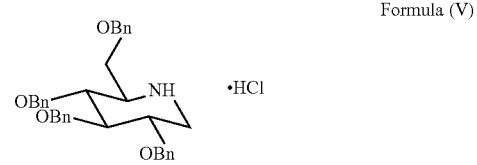

Formula (V)

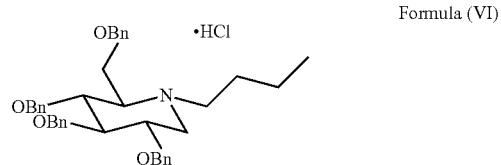

Formula (VI)

(2) reacting 2, 3, 4, 6-tetra-O-benzyl-N-butyl-1-deoxynojirimycin hydrochloride of formula (VI) with hydrogen in the presence of 10% Pd/C and HCl to produce miglustat hydrochloric salt;
(3) dissolving miglustat hydrochloric salt in a first solvent and adding an organic base;
(4) optionally removing the first solvent, and
(5) adding a second solvent to crystallize miglustat.

2. The process for the preparation of crystalline miglustat according to claim 1, wherein none of the steps (1) to (5) involves the use of any flash column chromatography or ion exchange column.

3. The process for the preparation of crystalline miglustat according to claim 1, wherein the first solvent is selected from the group consisting of water, methanol, ethanol, isopropanol, n-butanol, t-butanol, and a mixture of thereof.

4. The process for the preparation of crystalline miglustat according to claim 1, wherein the second solvent is selected from the group consisting of dichloromethane, ethyl acetate, diethyl ether, diisopropyl ether, isopropyl acetate, hexane, cyclohexane, heptane, and a mixture thereof.

5. The process for the preparation of crystalline miglustat according to claim 1, wherein the organic base is triethylamine, N,N-diisopropylethylamine, N-methylmorpholine, 1,8-diazabicycloundec-7-ene, or 1,5-diazabicyclonon-5-ene.

6. The process for the preparation of crystalline miglustat according to claim 1,
wherein the first solvent is methanol,
wherein the organic base is 1,8-diazabicycloundec-7-ene, and
wherein the second solvent is dichloromethane.

7. A process of preparing crystalline miglustat of formula (I) comprising the steps of:

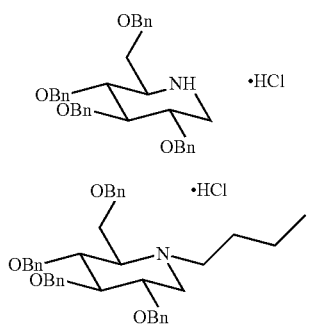

treating a solution of miglustat acid salt in a first solvent with an organic base, optionally removing the first solvent, and
adding a second solvent to crystallize miglustat of formula (I),
wherein no flash column chromatography or ion exchange column is used in the process.

8. The process of preparing crystalline miglustat according to claim 7,
wherein the miglustat acid salt is formed from miglustat reacting with an inorganic acid or an organic acid.

9. The process of preparing crystalline miglustat according to claim 8,
wherein the inorganic acid is selected from a group consisting of hydrochloric acid, sulfuric acid, phosphoric acid, and a mixture thereof, and
wherein the organic acid is selected from a group consisting of acetic acid, methanesulfonic acid, formic acid, citric acid, and a mixture thereof.

10. The process of preparing crystalline miglustat according to claim 7,
wherein the organic base is triethylamine, N,N-diisopropylethylamine, N-methylmorpholine, 1,8-diazabicycloundec-7-ene, or 1,5-diazabicyclonon-5-ene.

11. The process of preparing crystalline miglustat according to claim 7,
wherein the miglustat acid salt is miglustat hydrochloride, and
wherein the first solvent is selected from the group consisting of water, methanol, ethanol, isopropanol, n-butanol, t-butanol, and a mixture of thereof.

12. The process of preparing miglustat according to claim 7,
wherein the second solvent is selected from the group consisting of dichloromethane, ethyl acetate, diethyl ether, diisopropyl ether, isopropyl acetate, hexane, cyclohexane, heptane, and a mixture thereof.

* * * * *